(12) United States Patent
Neumann

(10) Patent No.: US 12,050,970 B2
(45) Date of Patent: *Jul. 30, 2024

(54) METHOD AND SYSTEM FOR SELECTING AN ALIMENTARY PROVIDER

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 857 days.

This patent is subject to a terminal disclaimer.

(21) Appl. No.: 17/088,207

(22) Filed: Nov. 3, 2020

(65) Prior Publication Data

US 2022/0138620 A1    May 5, 2022

(51) Int. Cl.
*G06Q 20/12*    (2012.01)
*G06F 16/2457*    (2019.01)
*G06F 16/29*    (2019.01)
*G06N 20/00*    (2019.01)
(Continued)

(52) U.S. Cl.
CPC ....... *G06N 20/00* (2019.01); *G06F 16/24578* (2019.01); *G06F 16/29* (2019.01); *G16H 40/20* (2018.01); *G16H 80/00* (2018.01)

(58) Field of Classification Search
CPC ... G06N 20/00; G06F 16/24578; G06F 16/29; G16H 40/20; G16H 80/00; G16H 50/20; G16H 50/70; G16H 20/60; G06Q 30/0261; G06Q 50/12; H04W 4/023
See application file for complete search history.

(56) References Cited

U.S. PATENT DOCUMENTS

| 8,595,050 B2* | 11/2013 | Scotto | G06Q 10/04 705/7.29 |
| 9,898,788 B1* | 2/2018 | Calargun | G06Q 50/12 |
| 9,934,530 B1 | 4/2018 | Square | |

(Continued)

OTHER PUBLICATIONS

Ridesahre Guy, https://www.youtube.com/watch?v=f2z_kncCuvo (Year: 2017).*

*Primary Examiner* — Hassan Mrabi
(74) *Attorney, Agent, or Firm* — Caldwell Intellectual Property Law

(57) ABSTRACT

A system for selecting an alimentary provider is disclosed. The system comprises a computing device configured to receive in input from a user device. Computing device is configured to generate a plurality of alimentary providers as a function of the input by identifying alimentary providers having a location within a threshold distance of the current geographical location of the user device. Computing device is configured to compute an alimentary combination factor for each alimentary provider as a function of a first machine-learning process. Computing device is configured to determine an alimentary combination assembly time and to select a transfer path to destination. Computing device is configured to output an alimentary combination total time. Computing device is configured to rank the plurality of alimentary providers as a function of decreasing alimentary combination factors and transmit the ranked plurality of alimentary providers. A method of selecting an alimentary provider is also disclosed.

20 Claims, 6 Drawing Sheets

(51) Int. Cl.
*G16H 40/20* (2018.01)
*G16H 80/00* (2018.01)

(56) References Cited

U.S. PATENT DOCUMENTS

| | | | |
|---|---|---|---|
| 10,366,436 B1 | 7/2019 | Kumar et al. | |
| 11,055,655 B1* | 7/2021 | Neumann | G06Q 10/08355 |
| 2013/0066665 A1* | 3/2013 | Tamhane | G06Q 30/02 |
| | | | 705/7.12 |
| 2014/0214590 A1* | 7/2014 | Argue | G06Q 30/0631 |
| | | | 705/26.7 |
| 2015/0161748 A1* | 6/2015 | Ratakonda | B01F 35/2207 |
| | | | 705/15 |
| 2015/0317582 A1* | 11/2015 | Nath | G06Q 10/06311 |
| | | | 705/7.13 |
| 2018/0018610 A1* | 1/2018 | Del Balso | G06N 3/08 |
| 2018/0233064 A1* | 8/2018 | Dunn | G09B 19/0092 |
| 2019/0228375 A1* | 7/2019 | Laury | G05D 1/0088 |
| 2019/0340537 A1* | 11/2019 | Fung | G06N 20/00 |
| 2022/0004955 A1* | 1/2022 | Neumann | G06F 16/285 |
| 2022/0028526 A1* | 1/2022 | Neumann | G06Q 10/1093 |
| 2022/0036215 A1* | 2/2022 | Neumann | G06Q 30/0282 |
| 2022/0121986 A1* | 4/2022 | Dohrn | G06F 16/24578 |
| 2022/0156083 A1* | 5/2022 | Neumann | G06F 9/3853 |

* cited by examiner

METHOD AND SYSTEM FOR SELECTING AN ALIMENTARY PROVIDER

FIELD OF THE INVENTION

The present invention generally relates to the field of artificial intelligence. In particular, the present invention is directed to a method and system for selecting an alimentary provider.

BACKGROUND

Users are often confronted with deciding where which restaurant would be more convenient to patronize and order food. After identifying an establishment, may be based on the proximity to the user's location, time is then wasted in dealing with selecting the food and placing an order as the user may have dietary restrictions, for example, which may extend the ordering activity further wasting more of the user's precious time.

SUMMARY OF THE DISCLOSURE

In an aspect, a system for selecting an alimentary provider is disclosed. The system comprises a computing device configured to receive an input from a user device at a current geographical location where the input includes an alimentary combination and a destination. The computing device is configured to generate a plurality of alimentary providers as a function of the input by identifying an alimentary provider at a location within a threshold distance relative to the current geographical location of the user device. Computing device is configured to compute a compute a plurality of alimentary combination factors as a function of a first machine-learning process trained by alimentary combination training data correlating alimentary combination factors to alimentary combinations, wherein each alimentary combination factor of the plurality of alimentary combination factors comprises a respective alimentary combination factor corresponding to the alimentary combination as prepared by an alimentary provider of the plurality of alimentary providers. The computing device is configured to determine a plurality of alimentary combination assembly times, wherein each alimentary combination assembly time of the plurality of alimentary combination assembly times comprises an alimentary combination assembly time corresponding to the alimentary combination as prepared by an alimentary provider of the plurality of alimentary providers. Computing device is configured to select a transfer path to the destination for the alimentary provider to the destination. The computing device is configured to output for each alimentary provider, an alimentary combination total time as a function of the alimentary combination assembly time and the transfer path associated with each provider and to rank each of the plurality of alimentary providers as a function of decreasing the respective alimentary combination factor and the respective alimentary combination total time associated with that alimentary provider. The computing device is configured to transmit the ranked plurality of alimentary providers.

In another aspect, a method for selecting an alimentary provider is disclosed. The method comprises receiving, by a computer device, an input from a user device at a current geographical location, wherein the input comprises an alimentary combination and a destination. The method generates, by a computer device, a plurality of alimentary providers as a function of the input by identifying alimentary providers at a location within a threshold distance relative to the current geographical location of the user device. The method comprises determining a a plurality of alimentary combination assembly times, wherein each alimentary combination assembly time of the plurality of alimentary combination assembly times comprises an alimentary combination assembly time corresponding to the alimentary combination as prepared by an alimentary provider of the plurality of alimentary providers. The method further comprises selecting a transfer path from the location of alimentary provider to the destination. The method outputs, by a computing device, for each provider, an alimentary combination total time as a function of the alimentary combination assembly time and the transfer path associated with each provider. The method comprises ranking each of the plurality of alimentary providers as a function of decreasing the respective alimentary combination factor and the respective alimentary combination total time associated with that alimentary provider. The computing device comprises transmitting the ranked plurality of alimentary providers.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for selecting an alimentary provider based on an input from a user. The user may enter an alimentary combination and a destination. Based on the input, a plurality of alimentary providers is generated. Also, based on the input and using a machine-learning process, an alimentary combination factor is generated for each alimentary provider which serves to rank the plurality of alimentary providers in, for example, a decreasing order where the highest alimentary combination factor and fastest time is outputted at the top.

The system and method for selecting an alimentary provider offers improvements as the user is able to for example, from a user device, select an alimentary provider from a list of alimentary providers that are ranked as a function of an alimentary combination factor which is based on inputting the alimentary combination.

Figure 1:
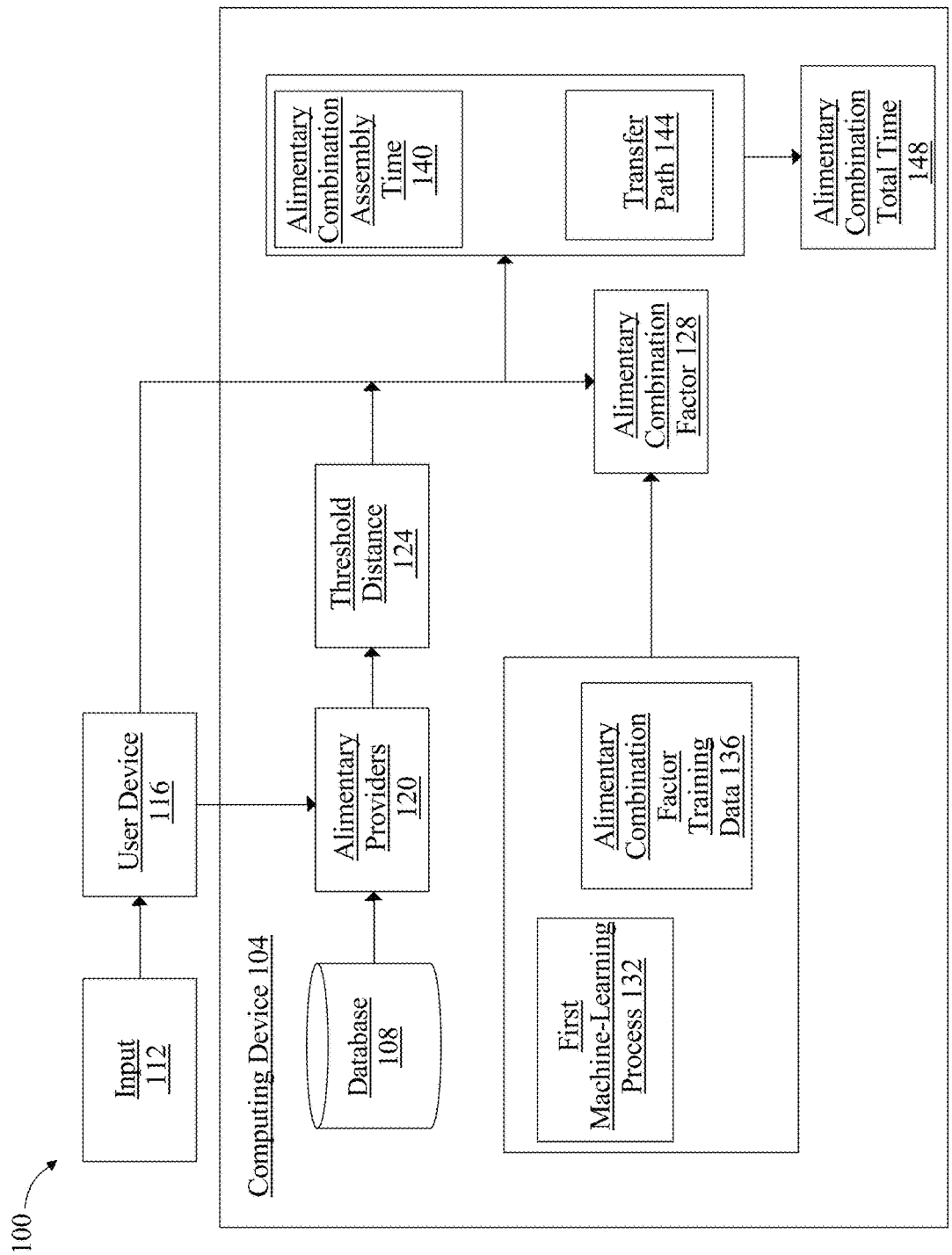
FIG. 1 is a block diagram of an exemplary embodiment of a system selecting an alimentary provider.

Referring now to FIG. 1, an exemplary embodiment of a system 100 for selecting an alimentary provider is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
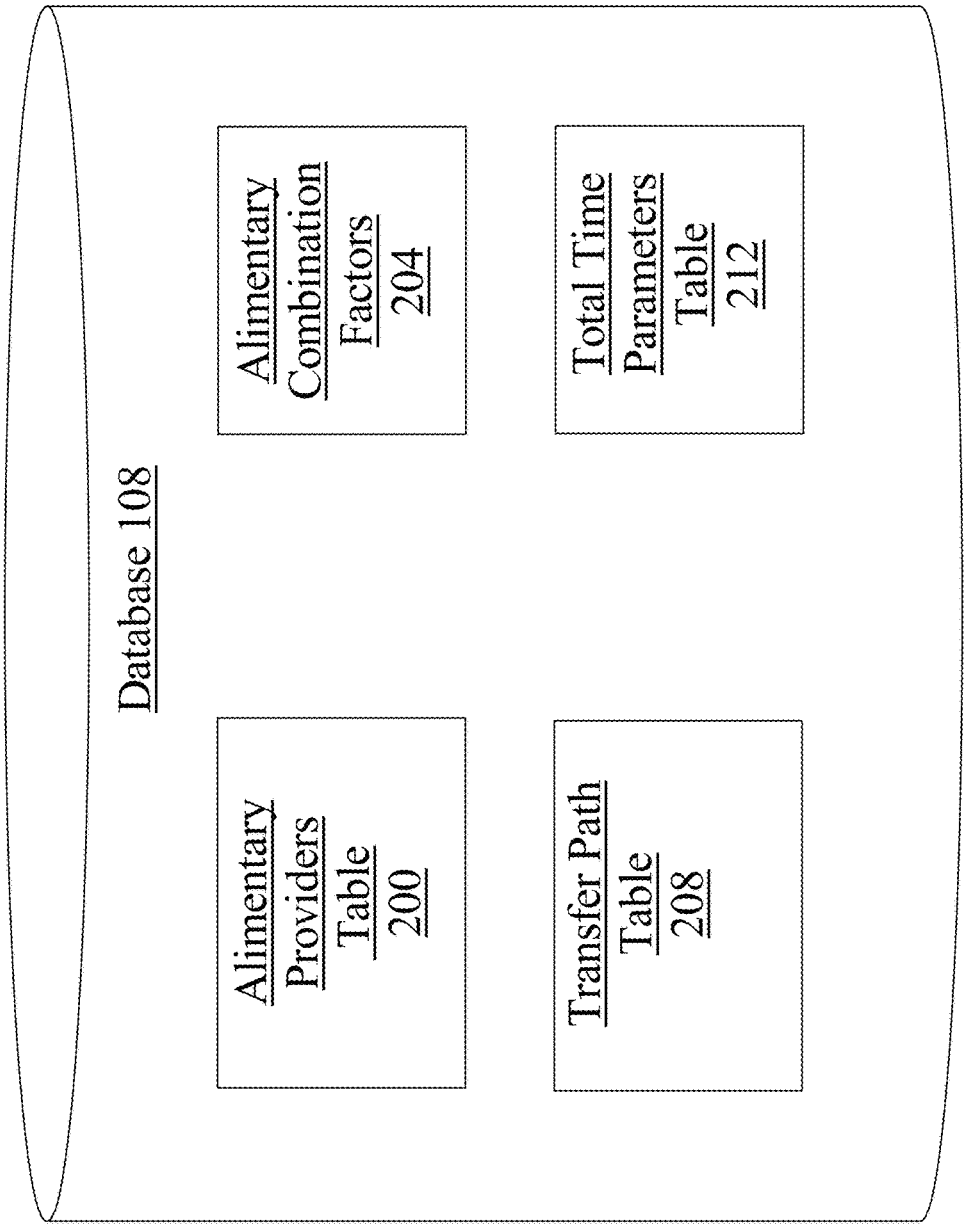
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, an alimentary provider table 200, which may be used to store records and attributes related to alimentary providers. This may include, but not limited to, names of alimentary providers, type of cuisine, or the like. As another non-limiting example, one or more tables in database 108 may include alimentary combination factor table 204 which may be used to store historical alimentary combination factor values of various alimentary combinations As another non-limiting example, one or more tables in database 108 may include a transfer path table 208. A transfer path table 208 may include, but not limited to historical information regarding paths between alimentary providers and destinations, historical conditions for the paths, and the like. As another non-limiting example, one or more tables in database 108 may include a total time parameters table 212. A total time parameters 212 may include parameters that may impact the transfer route, such as, but not limited to, potential detours due to activity in the transfer path, times where the path is likely to be congested, and the like.

Referring back to FIG. 1, computing device 104 is may receive an input 112 from a user device 116 at a current geographical location where the input 112 may include an alimentary combination and a destination. A "user device," as used in this disclosure, is any device that a user may use to enter an input. This may include, but it is not limited to, a cell phone, a tablet computer, a laptop computer, a desktop computer, and the like. User device 116 may have the capability to connect to the Internet. The user device may be configured to use a wireless network using Wi-Fi and any available communication standard such as, for example, IEEE 802.11. User device 116 may be configured to connect to a short-range network using, for example, Bluetooth® technology. User device 116 may be configured to access a network by connecting using a wired network connection using, for example, an Ethernet connection. Additionally, the user device may receive an input which may include an alimentary combination. An "alimentary combination," is defined for the purposes of this disclosure as a combination of ingredients that an alimentary provider and/or alimentary provider device indicates may be provided, for instance and without limitation in the form of a meal. As used in this disclosure, "alimentary providers" may include any entities that prepare alimentary combinations. As a non-limiting example, alimentary providers may prepare alimentary combinations at a restaurant. Other such alimentary providers may include any combination of one or more of the following: restaurants, bars, cafes, or other vendor of food or beverages, such as a hotel. A destination of the alimentary combination may be any location where the user may want to have the alimentary combination. For example, the user may want to have the alimentary combination delivered to a residence, or a business address may be chosen. Other examples of a destination for the alimentary combination include, but are not limited to an event, a college dormitory, or the like. As an example, a user may order a pepperoni pizza from a pizza restaurant by interacting with user device 116. User may select to have the pizza delivered to a destination for the alimentary combination, such as but not limited to, the user's residence, the user's workplace, or the like. The delivery may take place by transfer party directly employed by the alimentary provider. A "transfer party," as defined in this disclosure, is a person and/or device that transports alimentary combinations to one or more users requesting alimentary combinations. Transfer party may be on foot, or traveling by vehicle, such as a car, scooter, bicycle, etc. One or more transfer parties may be directed to one or more alimentary providers to receive an order placed by users and deliver the orders to the users located at corresponding destinations, which may include without limitation residential or commercial addresses.

With continued reference to FIG. 1, in an embodiment, input 112 received from user device 116 may include a food-related ailment. As used in this disclosure, a food-related ailment is defined as any ailment suffered by a user as a result of consuming a certain alimentary combinations. An ailment may include an impact of a food on a user's current health status, diagnosis, disorder, risk of developing a future medical condition, predisposition to a disease and/or condition and the like. For example, an ailment may identify that a food such as broccoli may worsen a user's hypothyroidism, while a food such as seaweed salad may improve a user's hypothyroidism. An ailment may include an intolerance and/or an allergy to certain nutrimental artifacts. An intolerance may lead to digestive issues such as, but not limited to diarrhea, nausea, bloating, gas, vomiting, and the like. An allergy may cause hives, itchiness, swelling of the skin. An allergy may cause anaphylaxis. User may supply a result in supplying actual result values from, for example, a medical test and the like. User may supply a result from completing a questionnaire. A questionnaire may include direct questions as to a specific value of a result. A questionnaire may also ask questions where the answers to those questions may offer an indication as to a food intolerance. A questionnaire may be iterative and/or adaptive. For example, based on an answer by user, the questionnaire may generate a series of more questions in order to identify at least one food condition.

Still referring to FIG. 1, in another embodiment, input 112 received from user device 116 may include an alternate alimentary combination. An "alternate alimentary combination," as defined in this disclosure, is defined as a different alimentary combination from the original input. The alimentary combination may be a new alimentary combination different from the input.

Alternatively, the alternate alimentary combination may include a variation of ingredients from the original input. For example, "hamburger" may serve as an input where the alternate alimentary combination may include "beef" or "turkey," or a "lamb" hamburger.

With continued reference to FIG. 1, computing device 104 may generate a plurality of alimentary provider candidates 120 as a function of the input. Computing device 104 may identify alimentary provider candidates 120 having a location within a threshold distance 124 of the current geographical location of user device 116. As used in this disclosure, a "threshold distance" is a value, in miles, that is either manually entered by the user or automatically selected by computing device 104 based on user history which serves as the maximum distance between the alimentary provider candidates 120 and user device 116. In a non-limiting example, computer device 104 may default to a threshold distance 124 of "0.5 miles." Using threshold distance 124 of 0.5 miles will output alimentary provider candidates 120 as a function of the input which are within 0.5 miles of user device 116. The user may expand the threshold distance 124 to, for example, "10 miles" where computing device will output alimentary provider candidates 120 as a function of the input which are within 10 miles of user device 112. A user may enter a range of values for the threshold distance. For example, a user may enter "0.5-1.0 miles which will output alimentary provider candidates that are within 0.5 and 1.0 miles of user device 116.

Still with reference to FIG. 1, computing device 104 may compute an alimentary combination factor 128 from a plurality of alimentary combination factors where each alimentary combination factor of the plurality of alimentary combination factors may include a respective alimentary combination factor 128 corresponding to the alimentary combination as prepared by the plurality of alimentary providers 120 as a function of a first machine-learning process 132. First machine-learning process 132 may be trained by alimentary combination factor training data 136. Alimentary combination factor training data 136 correlates alimentary combination factors to alimentary combinations. An alimentary combination factor would be returned for each alimentary provider included in the plurality of alimentary providers. A "alimentary combination factor", as used in this disclosure, is a numerical value assigned to an alimentary combination that represents the degree of nutritional value in an alimentary combination. For example, an alimentary combination that includes vegetables may receive a higher alimentary combination factor 128 than an alimentary combination that includes mostly fatty foods. A user may enter a range of alimentary combination factor values. In this example, computing device 104 may return alimentary combinations that have a alimentary combination factor value within the range specified by the user.

Figure 3:
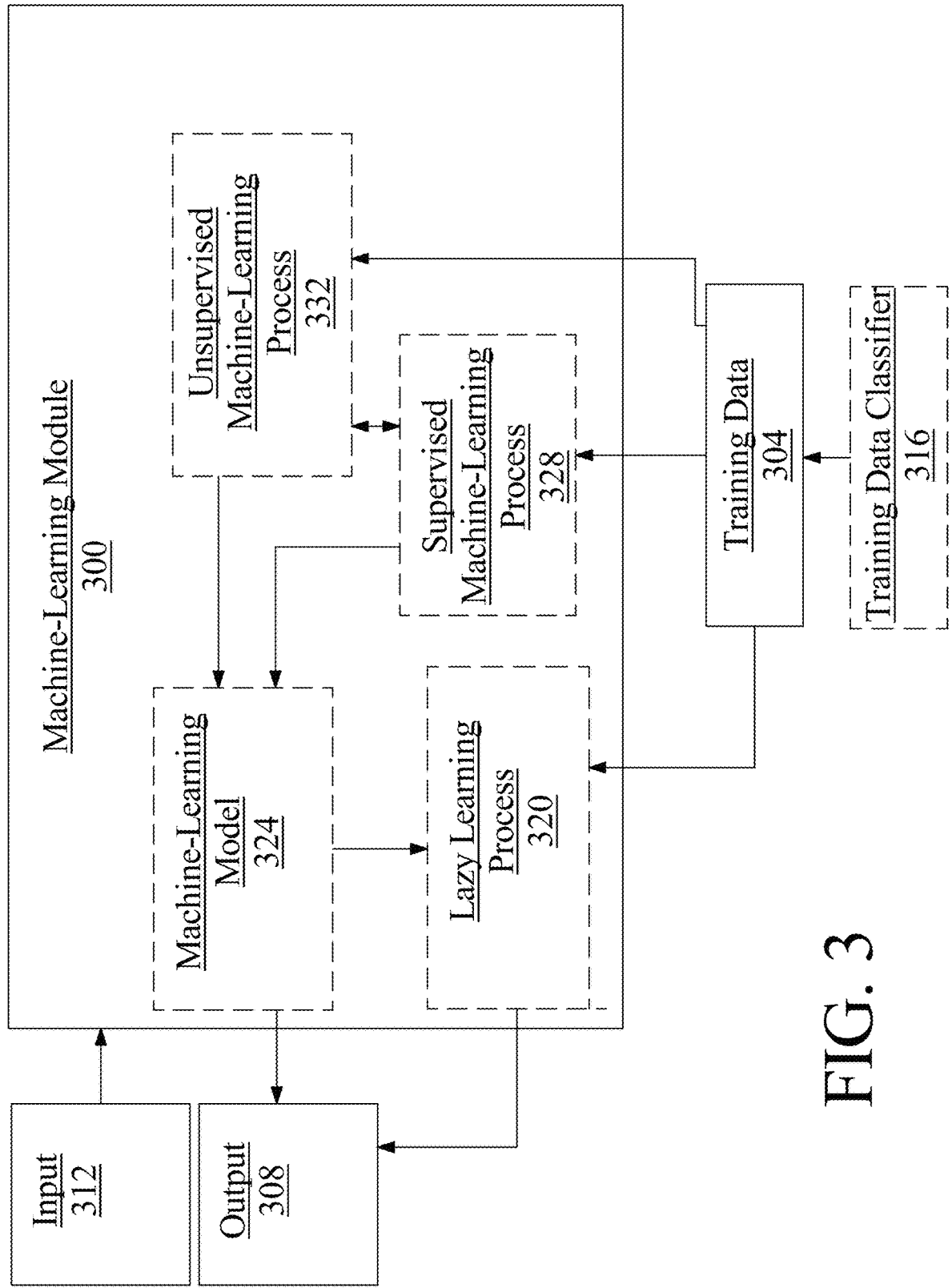
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify alimentary combinations with a particular alimentary combination factor that a person with diabetes may consume.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an alimentary combination as described above as inputs, an alimentary combination assembly time as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbor algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring back to FIG. 1, computing device 104 may determine an alimentary combination assembly time 140 where each alimentary combination assembly time 140 comprises an alimentary combination assembly time 140 corresponding to the alimentary combination as prepared by an alimentary provider of the plurality of alimentary providers 120. As used in this disclosure, an "alimentary combination assembly time" is defined as the time it may take any alimentary provider candidate to prepare an alimentary combination." Alimentary combination assembly time 140 may include the time it may take to collect the ingredients to prepare the alimentary combination; the time it takes to assemble or cook the alimentary combination; and the time it may take to box or bag the alimentary combination in order to transfer the alimentary combination to the user. Alternatively, to determine alimentary combination assembly time 140, a second machine-learning process may be trained using assembly time training data which correlates alimentary combinations to assembly time. Alimentary combination assembly time 140 is determined as a function of the second machine-learning process and the alimentary combination. The use of machine-learning processes and training data have been described earlier in this disclosure.

With continued reference to FIG. 1, computing device 104 may select a transfer path 144 from the location of each alimentary provider of the plurality of alimentary providers to the destination for the alimentary combination. As used in this disclosure, a "transfer path" is defined as a path that a transfer party would take to deliver the alimentary combination from an alimentary provider to the destination of user device 116. The determination and optimization of transfer routes may be implemented, without limitation, as disclosed in U.S. Nonprovisional application Ser. No. 16/890,339, filed on Jun. 2, 2020, and entitled, "METHODS AND SYSTEMS FOR PATH SELECTION USING VEHICLE ROUTE GUIDANCE," and U.S. Nonprovisional application Ser. No. 16/919,573, filed on Jul. 2, 2020, and entitled "A METHOD AND SYSTEM FOR SELECTION OF A PATH DELIVERIES;" each of U.S. Nonprovisional application Ser. No. 16/890,339 and U.S. Nonprovisional application Ser. No. 16/919,573 is incorporated by reference herein in its entirety. Transfer path 144 may include a direct route that may include the use of highways and toll roads. Transfer path 144 may include a path that is designed for a transfer agent who may be riding a bicycle. Transfer path 144 may be impacted by a total time parameter. A total time parameter may include, but not limited to, the time of day for the transfer to occur, the impact of current traffic conditions, the current weather, or a combination thereof. A total time parameter may cause computing device 104 to create a new transfer path that may create a faster transfer to destination of the alimentary combination. The new transfer path may be fastest but may not be the shortest relative to distance.

Figure 4:
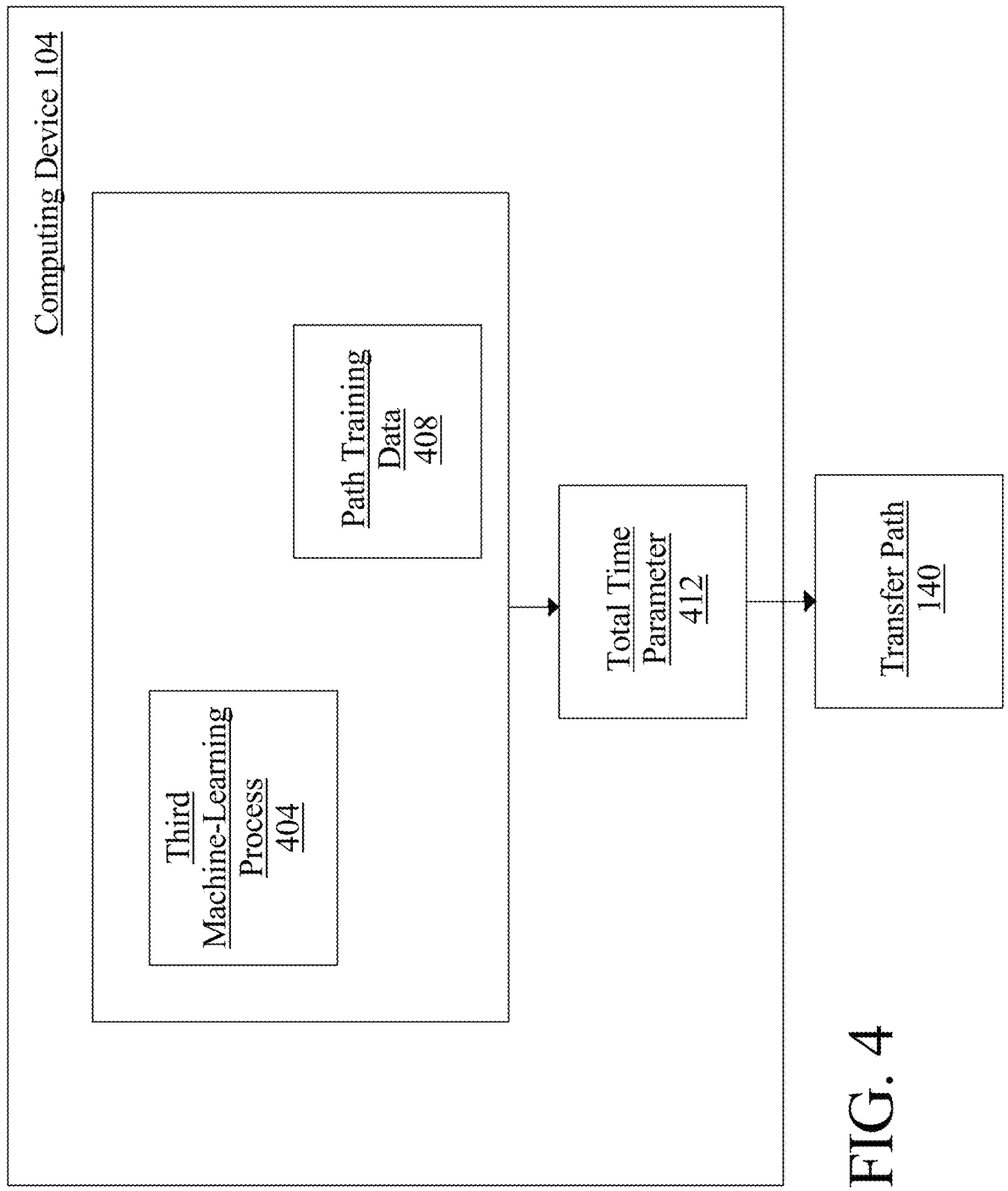
FIG. 4 is a block diagram of an exemplary embodiment of a determination of a transfer path.

Referring now to FIG. 4, an exemplary embodiment of the transfer path 144 selection process is illustrated. Computing device 104 may be configured to select transfer path 144 by training a third machine-learning process 404 using path training data 408. Path training data 408 correlates the current geographical location of alimentary provider with the destination. Selecting transfer path 144 includes receiving at least a total time parameter 412. Total time parameter 412 may include parameters regarding a time of day for a transfer, current traffic conditions, current weather, or a combination thereof. As an example, transfer path 140 may be selected for transfer of an alimentary combination to avoid rush hour or the effects of a heavy traffic load as a result of a traffic accident or construction. Alternatively, under such conditions, transfer path 144 may differ from a transfer path to the same destination under non-rush hour conditions or under traffic conditions not impacted by heavy traffic. Transfer path 144 is outputted as a function of at least the total time parameter 412 and the third machine-learning process 404. Once a transfer agent receives the selected transfer path 144, the transfer agent may decline the transfer path 144. Computing device 104 may select an alternate transfer path for the transfer agent.

Referring back to FIG. 1, in an embodiment, computing device 104 may be configured to pair the transfer path 144 with at least a transfer agent. Transfer agent may be on foot, or traveling by vehicle, such as a car, scooter, bicycle, or the like. One or more transfer agents may be directed to one or more alimentary providers to receive an order placed by users and deliver the orders to the users located at corresponding destinations, which may include without limitation residential or commercial addresses. Computing device 104 may pair a transfer path 144 with a transfer agent by identifying a plurality of currently active transfer agent and pairing transfer path 144 to a transfer agent of the plurality of active transfer agents. The plurality of currently active transfer agents may be included in, for example, an active transfer agent table in database 108. Alimentary providers 120 may also provide their own transfer agents that may be used to pair those transfer agents to a transfer path. Pairing of transfer path to a transfer party may involve, for example, determining the location of the transfer agent as a function of the alimentary provider and the location of the user device 116. Pairing of transfer path to transfer party may involve determining the load of the transfer agent. For example, a transfer agent may already have several transfers to fulfill whereas adding another transfer to the transfer agent may increase the time of transfer of all alimentary combinations. Pairing the route with a different transfer agent may help optimize transfer times.

With continued reference to FIG. 1, computing device 104 may be configured to output an alimentary combination total time 144 for each alimentary provider of the plurality of alimentary providers, as a function of alimentary combination assembly time 148 associated with that alimentary provider and transfer path 144. For example, computing device 104 may aggregate alimentary combination assembly time 148 and a projected time of transfer based on transfer path 144 to determine an alimentary combination total time 148. Alimentary combination total time 148 may include the time it may take to prepare, box, and pick up by transfer agent in combination for the time it may take a transfer agent to transfer the alimentary combination to the location of user device 116. In an embodiment, computing device 104 may be configured to display the geographical location of the plurality of alimentary providers as a function of the destination. As a non-limiting example, a user may visually see a pinpoint of the plurality of alimentary providers displayed in a map as a function of the destination. As such, a user may be able to see, visually, the location of all possible alimentary providers displayed in a map. The user may also be able to select an alimentary provider from the visual display. Additionally, the user may be able to see all available alimentary combination providers based on the geographical location and the distance between each alimentary provider.

Additionally, or alternatively, and with continued reference to FIG. 1, in another embodiment, computing device 104 may be configured to display the location of the transfer agent in the graphical user interface as a function of the destination. For example, user device 116 may receive a live status update about the location of the transfer agent selected to transfer the alimentary combination to the location of user device 116. The update may include a color depiction as to the status of the delivery as a function of the alimentary combination total time 148. As an example, the graphical user interface may show the transfer path in green if the transfer agent is on time to deliver the alimentary combination at the prescribed time based on the alimentary combination total time 148. In another non-limiting example, the graphical user interface may show the transfer path in yellow, if the time based on the alimentary combination total time is trending to a later delivery than the original delivery based on the alimentary combination total time. A yellow color may, in a non-limiting example, indicate a delivery time that is 5-15 later than the original delivery based on the alimentary combination total time. A red color may, for example, indicate a delivery time that is greater than 15 minutes than the original delivery based on the alimentary combination total time.

Additionally, or alternatively, and still referring to FIG. 1, computing device 104 may be configured to display in a graphical user interface of user device 116 the cost of the alimentary combination for the plurality of alimentary combination providers. As a non-limiting example, the user may be able to display the total cost of the item which may include the actual cost of the alimentary combination in addition to any transfer charges. Additionally, the user may be able to see a breakdown of the cost of the item. For example, a user may be able to see in the display the cost of the alimentary combination separate from the transfer charge. A user may be able to see in the display the cost of the alimentary combination and how much it may cost to have the item delivery by different transfer agents. In this example, the user is offered a selection of alimentary providers based on the input and a selection of a plurality of transfer agents to select.

Still referring to FIG. 1, computing device 104 may be configured to display an attribute about the alimentary combination. As used in this disclosure, an "attribute about the alimentary combination" is a descriptive information provided to the user about the alimentary combination. Attributes about the alimentary combination may include, but not limited to, a caloric value for the alimentary combination, a classification for the alimentary combination, which may include, but not limited to, if the alimentary combination is vegetarian, vegan, raw, or the like. The classification for the alimentary combination may include a descriptor indicating that the alimentary combination suits a particular diet such as Paleo®, Mediterranean, Atkins®, and the like. Additional attributes about the alimentary combination may include the serving size included in the alimentary combination, an image of the alimentary combination, and the like.

Still with reference to FIG. 1, computing device 104 may rank each of the plurality of alimentary providers 120 as a function of decreasing alimentary combination factor 128 and the respective alimentary combination total time 144 associated with alimentary provider. As an example, a dish that includes mostly or all vegetables and could be assembled and transferred the fastest would be ranked ahead of a dish that is mostly fried or contains mostly components regarded as unhealthy that may take a longer time to assemble and transferred. As a result, healthier dishes or those with a higher alimentary combination factor that may be transferred the fastest may be seen first in user device 116. In an embodiment, computing device may be configured to display the ranked plurality of alimentary providers in a graphical user interface in user device 116. A user, for example, may see the alimentary providers ranked by order of decreasing alimentary combination factor as the default display. The user may display the alimentary combination factor in increasing order with the lowest alimentary combination factor listed first. The user may also alternate between displaying the alimentary combination factors in increasing and decreasing order. Additionally, computing device 104 may be configured to display the ranked plurality of alimentary providers in the graphical user interface of user device 116 where the alimentary combination factor is above a certain threshold value. As an example, a user may only want to see alimentary providers with an alimentary combination factor of "greater than 75."

Additionally or alternatively, and with continued reference to FIG. 1, computing device may rank the plurality of alimentary providers 120 based on an objective function. An "objective function," as used in this disclosure, is a mathematical function used by a computing device 104 to score a quantitative element or factor which may include, for example, the alimentary combination factor for an alimentary provider or the transfer time from the provider to the destination. A machine-learning process may use, for instance, transfer time training data correlating alimentary provider and transfer path to transfer time and train a machine-learning model to output a plurality of transfer times based on alimentary provider and the transfer path. An objective function may then be optimized. In various embodiments a score of a particular factor may be based on a combination of one or more factors. Each factor may be assigned a score based on predetermined variables, for example, a preferred route may be scored higher than a non-preferred route. In some embodiments, the assigned scores may be weighted or unweighted. Computing device 104 may compute a score associated with each factor and select factors to minimize and/or maximize the score, depending on whether an optimal result is represented, respectively, by a minimal and/or maximal score. Objective function may be formulated as a linear objective function, which computing device 104 may solve using a linear program such as without limitation a mixed-integer program. A "linear program," as used in this disclosure, is a program that optimizes a linear objective function, given at least a constraint. For instance, an alimentary combination factor may be constrained to values resulting from an alimentary combination suitable for consumption with a user with a certain health condition. In various embodiments, system 100 may determine scores that maximizes a total score subject to at least a constraint.

With continued reference to FIG. 1, optimizing objective function may include minimizing a loss function, where a "loss function" is an expression an output of which an optimization algorithm minimizes to generate an optimal result. As a non-limiting example, computing device 104 may assign variables relating to a set of parameters, which may correspond to score components as described above, calculate an output of mathematical expression using the variables, and select score that produces an output having the lowest size, according to a given definition of "size," of the set of outputs representing each of plurality of candidate ingredient combinations; size may, for instance, included absolute value, numerical size, or the like. Selection of different loss functions may result in identification of different factors as generating minimal outputs.

Still referring to FIG. 1, computing device 104 may be configured to transmit the ranked plurality of alimentary providers 120. The ranked plurality of alimentary providers may be transmitted to a graphical user interface in user device 116 in, for example, a visual format. The ranked plurality of alimentary providers may be transmitted to user device 116 in audio format. For example, as the user may be unable to read the ranked plurality of alimentary providers displayed in a mobile phone as the user may be driving and against the law to use a mobile device, computing device 104 may be configured to read aloud the ranked list. Additionally, or alternatively, and still referring to FIG. 1, computing device 104 may be further configured to receive, from user device 116, user input requesting to order the alimentary combination from at least one alimentary provider from the plurality of alimentary providers. User device 116 may display to a user satisfactory results based on the input. User may interact with graphical display in user device 116 and cause, by touch for example, an order to be placed for an alimentary combination with at least one alimentary combination provider. Alternatively, user may interact with graphical display in user device 116 and cause, by voice using an enabled microphone feature, an order to be placed for an alimentary combination with at least one alimentary combination provider.

Additionally, or alternatively, and with continued reference to FIG. 1, in an embodiment, computing device 104 may be configured to received input from at least one alimentary provider indicating that the alimentary combination is unavailable. The alimentary combination may not be available, for example, if the ingredients required to prepare the alimentary combination are not available at an alimentary provider. In another non-limiting example, the order may have been placed outside of the business hours of the alimentary provider. In addition, the alimentary provider may be observing a holiday and may be closed at the time the order is placed. Computing device 104 may cause the order for the unavailable alimentary combination to be placed with a second alimentary provider. User device 116 may display a message indicating that the at least one alimentary provider is "unavailable." Additionally, user device 116 may display a message such as "using an alternate provider to fulfill your order." In another embodiment, computing device 104 may be configured to receive, from user device 116, user input rejecting the plurality of alimentary providers. A user may want to decline the plurality of alimentary providers offered and may reject the plurality of alimentary providers provided. Computing device 104 may receive a second input from user device 116. Input may include, a different alimentary combination and/ or a different destination.

Figure 5:
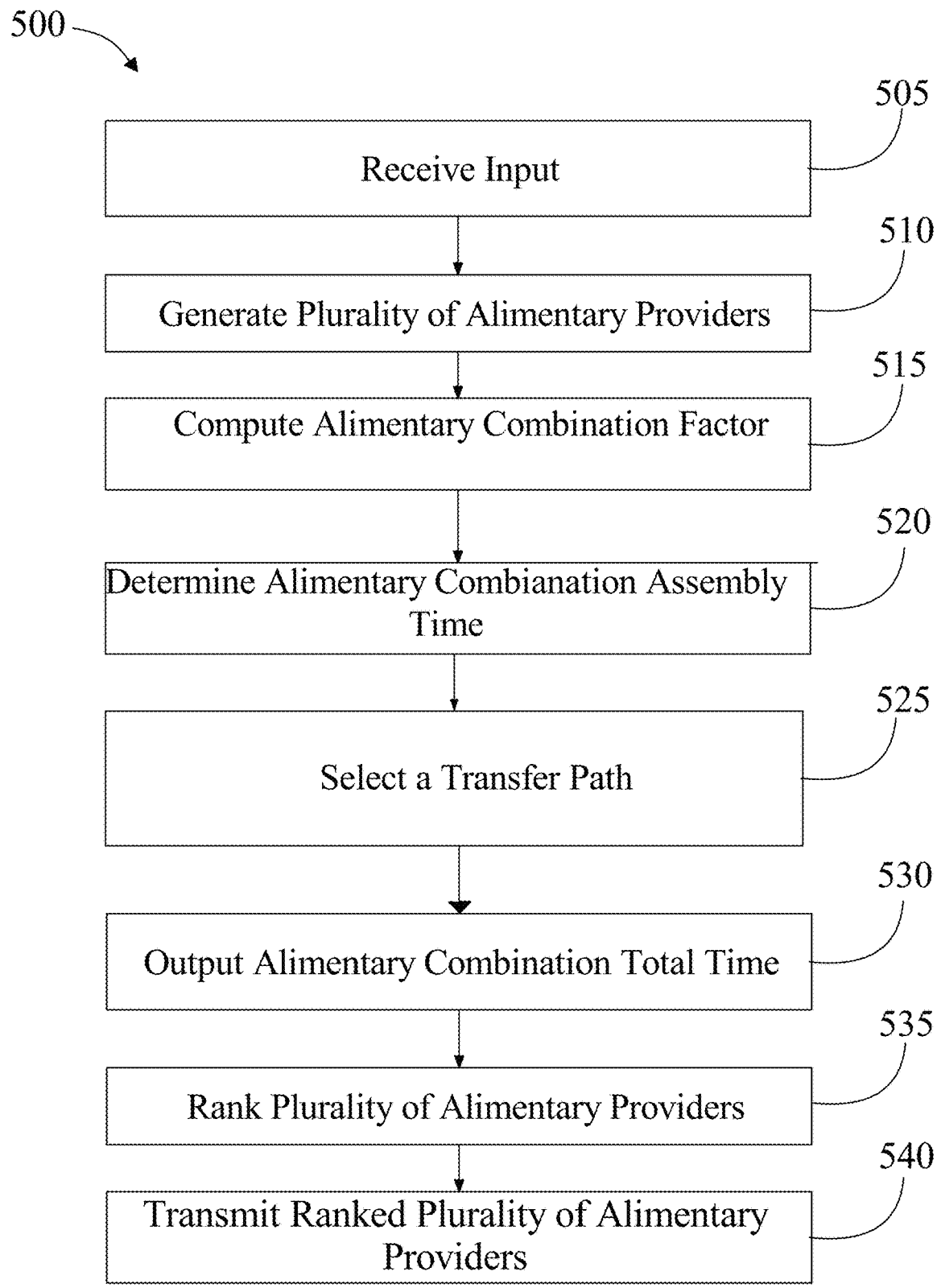
FIG. 5 is a flow diagram illustrating an exemplary embodiment of a method of selecting an alimentary provider.

Referring now to FIG. 5, an exemplary method 500 for selecting an alimentary provider is illustrated. At step 505, computing device receives an input from a user device at a current geographical location. The input includes an alimentary combination and a destination. In an embodiment, the input received from a user device may include a food-related ailment. In another embodiment, the input received from a user device may include an alternate alimentary combination. This step may be implemented, without limitation, as disclosed in FIGS. 1-4.

With continued reference to FIG. 5, at step 510, computing device may generate a plurality of alimentary providers as a function of the input by identifying an alimentary providers at a location within a threshold distance relative to the current geographical location of the user device. This step may be implemented, without limitation, as disclosed in FIGS. 1-4.

With continued reference to FIG. 5, at step 515, computing device may compute a plurality of alimentary combination factors as a function of a first machine-learning process trained by alimentary combination training data correlating alimentary combination factors to alimentary combinations, wherein each alimentary combination factor of the plurality of alimentary combination factors comprises a respective alimentary combination factor corresponding to the alimentary combination as prepared by an alimentary provider of the plurality of alimentary providers. This step may be implemented, without limitation, as disclosed in FIGS. 1-4.

Still referring to FIG. 5, at step 520, computing device may determine a plurality of alimentary combination assembly times, wherein each alimentary combination assembly time of the plurality of alimentary combination assembly times comprises an alimentary combination assembly time corresponding to the alimentary combination as prepared by an alimentary provider of the plurality of alimentary providers. This step may be implemented, without limitation, as disclosed in FIGS. 1-4.

Referring still to FIG. 5, at step 525, computing device may select a transfer path from the alimentary provider to the destination. This step may be implemented, without limitations, as described in FIGS. 1-4. In an embodiment, the method further includes pairing the transfer path with at least a transfer party, where the pairing further includes identifying a plurality of currently active transfer party and pairing the transfer path to a transfer party of the plurality of active transfer parties.

With continued reference to FIG. 5, at step 530, computing device may output an alimentary combination total time as a function of the alimentary combination assembly time and the transfer path for the alimentary provider. This may be implemented, without limitation, as described in FIGS. 1-4. In an embodiment, the computing device is configured to display the geographical location of an alimentary provider of the plurality of alimentary providers as a function of the destination in a geographical user interface of the user device. In another embodiment, the computing device may be configured to display the location of a transfer agent in the graphical user interface as a function of the destination. Additionally, computing device may be configured to display in a graphical user interface of user device the cost of each of the the alimentary combination ofthe plurality of alimentary combination providers. As a non-limiting example, the user may be able to display the total cost of the item which may include the actual cost of the alimentary combination in addition to any transfer charges. Computing device may be configured to display an attribute about the alimentary combination. As used in this disclosure, an "attribute about the alimentary combination" is a descriptive information provided to the user about the alimentary combination. Attributes about the alimentary combination may include, but not limited to, a caloric value for the alimentary combination, a classification for the alimentary combination, which may include, but not limited to, if the alimentary combination is vegetarian, vegan, raw, or the like. The classification for the alimentary combination may include a descriptor indicating that the alimentary combination suits a particular diet such as Paleo®, Mediterranean, Atkins®, and the like. Additional attributes about the alimentary combination may include the serving size included in the alimentary combination, an image of the alimentary combination, and the like. This may be implemented, without limitation, as described in FIGS. 1-4.

Still referring to FIG. 5, at step 535, computing device may rank each of the plurality of alimentary providers as a function of decreasing the respective alimentary combination factor and the respective alimentary combination total time associated with that alimentary provider. This may be implemented as described in FIGS. 1-4.

With continued reference to FIG. 5, at step 540, computing device may be configured to transmit the ranked plurality of alimentary providers. This may be implemented, without limitation, as described in FIGS. 1-4. In an embodiment, the computing device may be configured to display the ranked plurality of alimentary providers in a graphical user interface of the user device. Additionally, the computing device may be further configured to receive, from the user device, a user input requesting to order the alimentary combination from at least one alimentary provider from the plurality of alimentary providers. Computing device may cause an order for the alimentary combination to be placed with the at least one alimentary provider. Additionally, or alternatively, in another embodiment, computing device may be configured to received an input from at least one alimentary provider indicating that the alimentary combination is unavailable. The alimentary combination may not be available, for example, if the ingredients required to prepare the alimentary combination are not available at an alimentary provider. Computing device may cause an order for the unavailable alimentary combination to be placed with a second alimentary provider. In a further embodiment, the computing device may be configured to receive, from user device, user input rejecting the plurality of alimentary providers. A user may want to decline the plurality of alimentary providers offered and may reject the plurality of alimentary providers provided. The computing device may receive a second input from user device as a function of the rejection. Input may include a different alimentary combination and/or a different destination.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
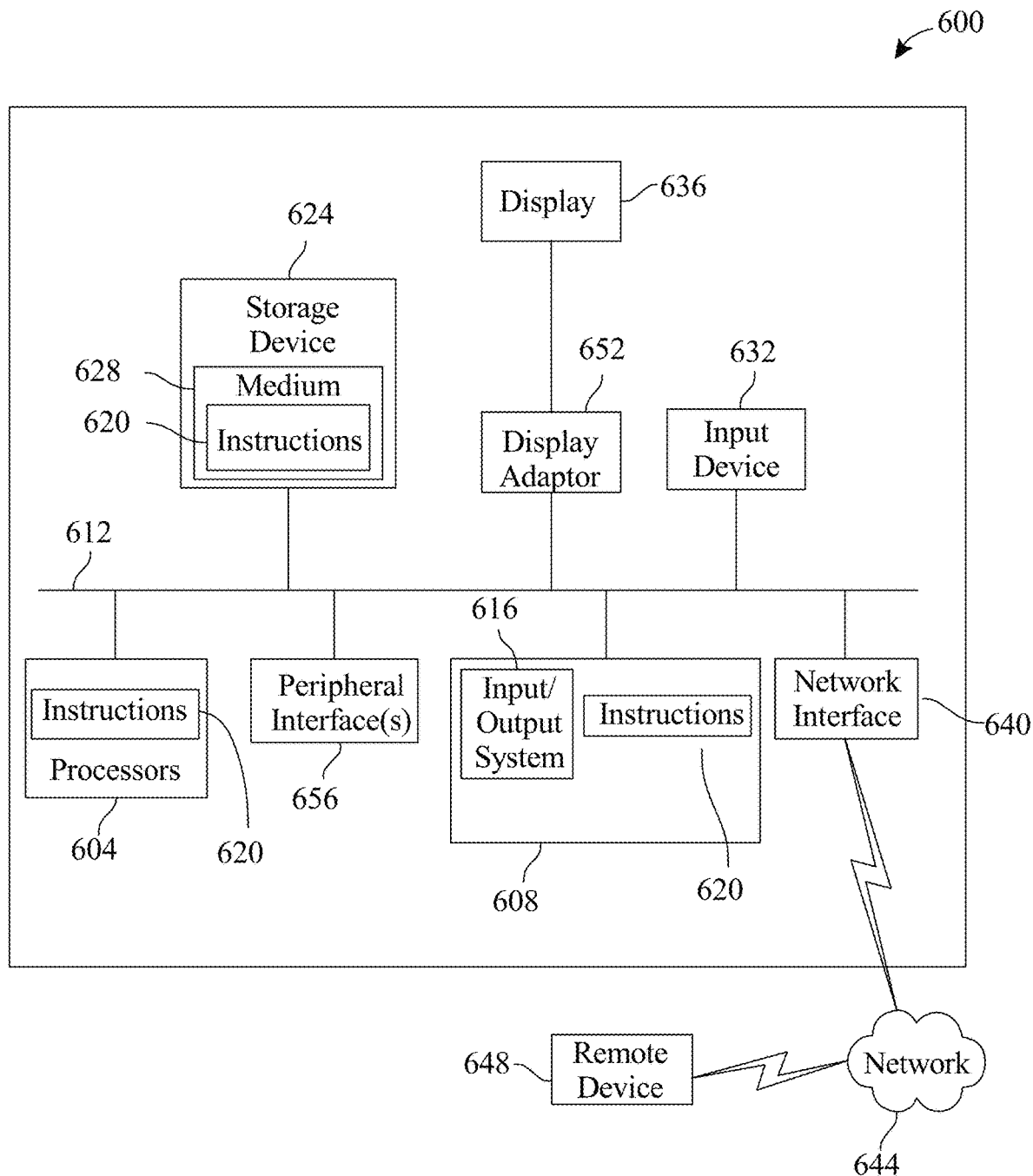
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for selecting an alimentary provider, the system comprising:
   a computing device comprising a processor and a memory configured to:

receive an input from a user device at a current geographical location, wherein the input comprises:
    an alimentary combination including a food-related ailment comprising a user's risk of developing a future medical condition; and
    a destination;
generate a plurality of alimentary providers as a function of the input by identifying an alimentary provider at a location within a threshold distance relative to the current geographical location of the user device;
compute a plurality of alimentary combination factors as a function of a first machine-learning process trained by alimentary combination training data correlating alimentary combination factors to alimentary combinations, wherein each alimentary combination factor of the plurality of alimentary combination factors comprises a respective alimentary combination factor corresponding to the alimentary combination as prepared by an alimentary provider of the plurality of alimentary providers;
determine a plurality of alimentary combination assembly times, wherein each alimentary combination assembly time of the plurality of alimentary combination assembly times comprises an alimentary combination assembly time corresponding to the alimentary combination as prepared by an alimentary provider of the plurality of alimentary providers;
select a transfer path from the location of each alimentary provider of the plurality of alimentary providers to the destination;
output, for each alimentary provider of the plurality of alimentary providers, an alimentary combination total time as a function of the alimentary combination assembly time and the transfer path associated with that alimentary provider;
rank each of the plurality of alimentary providers as a function of decreasing the respective alimentary combination factor and the respective alimentary combination total time associated with that alimentary provider; and
transmit the ranked plurality of alimentary providers.

2. The system of claim 1, wherein the input received from the user device further comprises a food-related ailment.

3. The system of claim 1, wherein the input received from the user device further comprises an alternate alimentary combination.

4. The system of claim 1, wherein the computing device is further configured to pair the transfer path with at least a transfer agent, wherein pairing the transfer path further comprises:
    identifying a plurality of currently active transfer agents; and
    pairing the transfer path to a transfer agent of the plurality of active transfer agents.

5. The system of claim 1, wherein the computing device is further configured to display the ranked plurality of alimentary providers in a graphical user interface of the user device.

6. The system of claim 1, wherein the computing device is further configured to display a geographical location of an alimentary provider of the plurality of alimentary providers as a function of the destination in a graphical user interface of the user device.

7. The system of claim 1, wherein the computing device is further configured to display a location of a transfer agent as a function of the destination in a graphical user interface in the user device.

8. The system of claim 1, wherein the computing device is further configured to:
    receive, from the user device, a user input requesting to order the alimentary combination from at least one alimentary provider from the plurality of alimentary providers; and
    cause an order for the alimentary combination to be placed with the at least one alimentary combination provider.

9. The system of claim 8, wherein the computing device is further configured to:
    receive an input, from the at least one alimentary provider, wherein the alimentary combination ordered is unavailable; and
    cause an order for the unavailable alimentary combination to be placed with a second alimentary provider.

10. The system of claim 1, wherein the computing device is further configured to:
    receive, from the user device, a user input rejecting the plurality of alimentary provider candidates; and
    receive a second input from the user device as a function of the rejection.

11. A method for selecting an alimentary provider, the method comprising:
    receiving, by a computing device, an input from a user device at a current geographical location, wherein the input comprises:
        an alimentary combination including a food-related ailment comprising user's risk of developing a future medical condition; and
        a destination;
    generating, by the computing device, a plurality of alimentary providers as a function of the input by identifying alimentary providers at a location within a threshold distance relative to the current geographical location of the user device;
    computing, by the computing device, a plurality of alimentary combination factors as a function of a first machine-learning process trained by alimentary combination training data correlating alimentary combination factors to alimentary combinations, wherein each alimentary combination factor of the plurality of alimentary combination factors comprises a respective alimentary combination factor corresponding to the alimentary combination as prepared by an alimentary provider of the plurality of alimentary providers;
    determining, by the computing device, a plurality of alimentary combination assembly times, wherein each alimentary combination assembly time of the plurality of alimentary combination assembly times comprises an alimentary combination assembly time corresponding to the alimentary combination as prepared by an alimentary provider of the plurality of alimentary providers;
    selecting, by the computing device a transfer path from the location of each alimentary provider of the plurality of alimentary providers to the destination;
    outputting, by the computing device, for each alimentary provider of the plurality of alimentary providers, an alimentary combination total time as a function of the alimentary combination assembly time and the transfer path associated with that alimentary provider;

ranking, by the computing device, each of the plurality of alimentary providers as a function of decreasing the respective alimentary combination factor and the respective alimentary combination total time associated with that alimentary provider; and transmitting, by the computing device, the ranked plurality of alimentary providers.

12. The method of claim 11, wherein the input received from the user device further comprises a food-related ailment.

13. The method of claim 11, wherein the input received from the user device further comprises an alternate alimentary combination.

14. The method of claim 11, wherein the computing device is further configured to pair the transfer path with at least a transfer agent, wherein pairing the transfer path further comprises:

identifying a plurality of currently active transfer agent; and pairing the transfer path to a transfer agent of the plurality of active transfer agents.

15. The method of claim 11, wherein the computing device is further configured to display the ranked plurality of alimentary providers in a graphical user interface of the user device.

16. The method of claim 11, wherein the computing device is further configured to display a geographical location of an alimentary provider of the plurality of alimentary providers as a function of the destination in a graphical user interface of the user device.

17. The method of claim 11, wherein the computing device is further configured to display a location of a transfer agent as a function of the destination in a graphical user interface in the user device.

18. The method of claim 11, wherein the computing device is further configured to:

receive, from the user device, a user input requesting to order the alimentary combination from at least one alimentary provider from the plurality of alimentary providers; and cause an order for the alimentary combination to be placed with the at least one alimentary combination provider.

19. The method of claim 18, wherein the computing device is further configured to:

receive input, from the at least one alimentary provider, wherein the alimentary combination ordered is unavailable; and cause an order for the unavailable alimentary combination to be placed with a second alimentary provider.

20. The method of claim 11, further comprising:

receiving, from the user device, a user input rejecting the plurality of alimentary provider candidates; and receiving a second input from the user device as a function of the rejection.

\* \* \* \* \*